(12) United States Patent
Gross et al.

(10) Patent No.: US 6,403,857 B1
(45) Date of Patent: Jun. 11, 2002

(54) ABSORBENT STRUCTURES WITH INTEGRAL LAYER OF SUPERABSORBENT POLYMER PARTICLES

(75) Inventors: James R. Gross, Cordova; Samuel C. Baer, Germantown, both of TN (US); Steve Leptick, Delta (CA); John P. Erspamer, Bartlett, TN (US)

(73) Assignee: Buckeye Technologies Inc., Memphis, TN (US)

( * ) Notice: Subject to any disclaimer, the term of this patent is extended or adjusted under 35 U.S.C. 154(b) by 0 days.

(21) Appl. No.: 09/211,935

(22) Filed: Dec. 15, 1998

Related U.S. Application Data
(60) Provisional application No. 60/088,451, filed on Jun. 8, 1998.

(51) Int. Cl.[7] .................................................. A61F 13/15
(52) U.S. Cl. ........................ 604/365; 604/367; 604/366; 604/368; 604/370; 604/372
(58) Field of Search ............................. 604/368, 385.2, 604/366, 385.1, 365, 367, 370, 378, 375, 372, 376; 525/330.1; 206/440; 264/342

(56) References Cited

U.S. PATENT DOCUMENTS

| | | | |
|---|---|---|---|
| 2,929,154 A | * 3/1960 | Finnegan | |
| 3,224,986 A | * 12/1965 | Butler et al. | 260/9 |
| 3,332,909 A | * 7/1967 | Farnham et al. | 260/47 |
| 3,660,431 A | * 5/1972 | Hatch et al. | 260/332.3 |
| 3,669,103 A | * 6/1972 | Harper et al. | 128/156 |
| 3,749,738 A | * 7/1973 | Hatch et al. | 260/332.3 |
| 3,898,311 A | * 8/1975 | Mtchell et al. | 264/103 |
| 3,980,663 A | * 9/1976 | Gross | 260/29.6 |
| 3,993,616 A | 11/1976 | Gross | 260/29.4 |
| 4,056,103 A | 11/1977 | Kaczmarzyk et al. | 128/285 |
| 4,076,673 A | * 2/1978 | Burkholder, Jr. | 260/29.2 |
| 4,084,033 A | 4/1978 | Drelich | 428/198 |
| 4,117,184 A | 9/1978 | Erickson et al. | 428/224 |
| 4,335,722 A | * 6/1982 | Jackson | 128/285 |
| 4,342,858 A | * 8/1982 | Herman et al. | 526/317 |
| 4,364,992 A | 12/1982 | Ito et al. | 428/283 |
| 4,410,571 A | 10/1983 | Korpman | 427/385.5 |
| 4,424,247 A | 1/1984 | Erickson | 428/138 |
| 4,444,830 A | 4/1984 | Erickson | 428/246 |
| RE31,822 E | 2/1985 | Erickson et al. | 128/156 |
| 4,529,739 A | 7/1985 | Scott et al. | 521/72 |
| 4,559,243 A | 12/1985 | Pässler et al. | 427/209 |
| 4,578,068 A | * 3/1986 | Kramer et al. | 604/368 |
| 4,596,567 A | * 6/1986 | Iskra | 604/368 |

(List continued on next page.)

FOREIGN PATENT DOCUMENTS

| | | |
|---|---|---|
| EP | 0 689 817 A2 | 1/1996 |
| EP | 0689817 A2 * | 1/1996 |
| EP | 0 690 077 A1 | 1/1996 |
| EP | 0690077 A1 * | 1/1996 |
| WO | WO 94/22940 A | 10/1994 |
| WO | 94/22940 * | 10/1994 |

OTHER PUBLICATIONS

Journal of Applied Polymer Science, vol. 17–No. 3, pp. 721–735, Mar. 1973.*

Carr et al., Interpolymer from Starch Xanthate and Polyamide–Polyamine–Epichlorohydrin Resin: Structure and Papermaking Application, Journal of Applied Polymer Science, 17:721–735 (1973).

*Primary Examiner*—John G. Weiss
*Assistant Examiner*—Paul Shanoski
(74) *Attorney, Agent, or Firm*—Darby & Darby

(57) ABSTRACT

A discrete superabsorbent layer is adhered to the lower surface of a fibrous absorbent structure using a water-based polymeric binder is disclosed. The advantages are that a superabsorbent roll good can be prepared for later conversion into disposable absorbent products. The use of the water-based polymeric binder prevents particles of superabsorbent from becoming dislodged from the structure during handling and processing.

22 Claims, 1 Drawing Sheet

U.S. PATENT DOCUMENTS

| | | | | |
|---|---|---|---|---|
| 4,627,847 A | * | 12/1986 | Puletti et al. | 604/366 |
| 4,645,789 A | | 2/1987 | Dabi | 524/379 |
| 4,649,164 A | | 3/1987 | Scott, et al. | 521/149 |
| 4,673,402 A | * | 6/1987 | Weisman et al. | 604/368 |
| 4,721,647 A | | 1/1988 | Nakanishi et al. | 428/283 |
| 4,773,903 A | | 9/1988 | Weisman et al. | 604/368 |
| 4,813,945 A | | 3/1989 | Le-Khac | 604/367 |
| 4,888,231 A | * | 12/1989 | Angstadt | 428/213 |
| 4,892,533 A | | 1/1990 | Le-Khac | 604/368 |
| 4,914,170 A | | 4/1990 | Chang et al. | 526/240 |
| 4,933,390 A | * | 6/1990 | Dabi et al. | 524/808 |
| 5,009,650 A | * | 4/1991 | Bernardin | 604/378 |
| 5,041,104 A | * | 8/1991 | Seal | 604/367 |
| 5,057,166 A | * | 10/1991 | Young, Sr. et al. | 156/62.2 |
| 5,061,235 A | | 10/1991 | Hogan | 600/21 |
| 5,064,689 A | | 11/1991 | Young, Sr. et al. | 427/202 |
| 5,100,397 A | | 3/1992 | Poccia et al. | 604/365 |
| 5,128,082 A | * | 7/1992 | Makoui | 264/112 |
| 5,135,792 A | * | 8/1992 | Hogan | 428/74 |
| 5,147,343 A | * | 9/1992 | Kellenberger | 604/368 |
| 5,161,686 A | * | 11/1992 | Weber et al. | 206/440 |
| 5,176,668 A | * | 1/1993 | Bernardin | 604/368 |
| 5,176,670 A | | 1/1993 | Roessler et al. | 604/391 |
| 5,188,624 A | | 2/1993 | Young, Sr. et al. | 604/378 |
| 5,230,959 A | | 7/1993 | Young, Sr. et al. | 428/372 |
| 5,234,423 A | * | 8/1993 | Alemany et al. | 604/385.2 |
| 5,248,309 A | * | 9/1993 | Serbiak et al. | 604/368 |
| 5,268,419 A | | 12/1993 | Stack et al. | 524/831 |
| 5,300,192 A | | 4/1994 | Hansen et al. | 162/184 |
| 5,308,896 A | | 5/1994 | Hansen et al. | 524/13 |
| 5,336,554 A | | 8/1994 | Knight | 428/230 |
| 5,338,766 A | | 8/1994 | Phan et al. | 521/63 |
| 5,352,480 A | | 10/1994 | Hansen et al. | 427/202 |
| 5,378,528 A | * | 1/1995 | Makoui | 428/219 |
| 5,389,181 A | * | 2/1995 | Vukos et al. | 156/264 |
| 5,422,169 A | * | 6/1995 | Roe | 428/212 |
| 5,432,000 A | | 7/1995 | Young, Sr. et al. | 428/372 |
| 5,447,977 A | | 9/1995 | Hansen et al. | 524/13 |
| 5,498,478 A | | 3/1996 | Hansen et al. | 428/372 |
| 5,516,585 A | | 5/1996 | Young, Sr. et al. | 428/372 |
| 5,522,810 A | * | 6/1996 | Allen, Jr. et al. | 604/366 |
| 5,538,783 A | | 7/1996 | Hansen et al. | 428/283 |
| 5,543,215 A | | 8/1996 | Hansen et al. | 428/283 |
| 5,547,541 A | | 8/1996 | Hansen et al. | 162/12 |
| 5,547,745 A | | 8/1996 | Hansen et al. | 428/283 |
| 5,558,658 A | | 9/1996 | Menard et al. | 604/385.1 |
| 5,571,618 A | | 11/1996 | Hansen et al. | 428/359 |
| 5,589,256 A | | 12/1996 | Hansen et al. | 428/283 |
| 5,591,149 A | | 1/1997 | Cree et al. | 604/378 |
| 5,597,873 A | * | 1/1997 | Chambers et al. | 525/330.1 |
| 5,607,414 A | * | 3/1997 | Richards et al. | 604/378 |
| 5,607,759 A | | 3/1997 | Hansen et al. | 442/417 |
| 5,611,885 A | | 3/1997 | Hansen et al. | 156/326 |
| 5,614,570 A | | 3/1997 | Hansen et al. | 524/13 |
| 5,641,561 A | | 6/1997 | Hansen et al. | 442/417 |
| 5,645,542 A | | 7/1997 | Anjur et al. | 604/368 |
| 5,672,418 A | | 9/1997 | Hansen et al. | 428/283 |
| 5,693,411 A | * | 12/1997 | Hansen | 428/283 |
| 5,763,067 A | | 6/1998 | Bruggemann et al. | 428/317.9 |
| 5,789,326 A | | 8/1998 | Hansen et al. | 442/59 |
| 5,800,419 A | | 9/1998 | Soga et al. | 604/368 |
| 5,807,364 A | | 9/1998 | Hansen et al. | 604/367 |
| 5,830,202 A | | 11/1998 | Bogdanski et al. | 604/378 |
| 5,844,039 A | | 12/1998 | Scranton et al. | 524/530 |
| 5,859,074 A | | 1/1999 | Rezai et al. | 521/54 |
| 5,938,650 A | | 8/1999 | Baer et al. | 604/368 |
| 5,944,706 A | | 8/1999 | Palumbo et al. | 604/368 |
| 5,977,014 A | | 11/1999 | Plischke et al. | 502/401 |
| 5,998,312 A | | 12/1999 | Kroesbergen | 442/221 |

* cited by examiner

ABSORBENT STRUCTURES WITH INTEGRAL LAYER OF SUPERABSORBENT POLYMER PARTICLES

This patent application claims priority under 35 U.S.C. §119 from the expired provisional application Ser. No. 60/088,451 filed Jun. 8, 1998, incorporated herein by reference in its entirety.

FIELD OF THE INVENTION

The present invention relates to a process for preparing a superabsorbent roll good for use in disposable absorbent hygiene articles such as diapers and sanitary napkins and to the products of the process. A water-based binder, preferably foamed, is combined with conventional superabsorbent particles to form a discrete but integral superabsorbent layer on the surface of a fibrous absorbent structure. When used in disposable absorbent products, the integral superabsorbent layer is located away from the intended fluid insult. The insult side of such disposable absorbent product preferably contains an acquisition layer of bonded stiffened cellulosic or synthetic fibers bonded with thermoplastic binder fibers or powder, a latex binder, or a combination thereof.

BACKGROUND OF THE INVENTION

Conventional absorbent articles such as baby diapers, adult incontinence devices, and feminine napkins are typically made with a cellulose fiber fluff-based absorbent core sandwiched between a liquid pervious top sheet whose function is to allow the unobstructed passage of fluid to the absorbent core, and a liquid impervious backing sheet usually of plastic material, whose function is to contain the absorbed fluid and prevent it from passing through the absorbent core and soiling the undergarments of the wearer of the absorbent article.

The absorbent core of these absorbent articles is typically constructed of defiberized wood pulp with or without superabsorbent polymer granules. The absorbent core is typically formed on a pad-forming unit of a converting machine on a carrier tissue to facilitate processing. Some absorbent core-forming units are equipped with layering capability in which a second discrete fluff layer may be laid over a primary fluff-based absorbent layer to form a multi-layer absorbent structure. In these absorbent structures, the primary layer may include superabsorbent polymer granules. With regard to conventionally produced absorbent structures, reference is made to U.S. Pat. Nos. 5,009,650, 5,378,528, 5,128,082, 5,607,414, 5,147,343, 5,149,335, 5,522,810, 5,041,104, 5,176,668, 5,389,181 and 4,596,567, the disclosures of which are hereby incorporated herein by reference.

In recent years, market demand for thinner and more comfortable absorbent articles has increased. Ultra-thin feminine napkins are no longer constructed from loose wood pulp, which tends to give a bulky product, but with roll good based airlaid absorbent cores in which a roll of preformed absorbent core material is unwound directly onto the absorbent pad-making machine without the defiberization step required for fluff-based products. The roll-goods based approach results in a product thinness not possible by loose fluff-based technology.

With respect to the superabsorbent polymer component of absorbent structures, it is known in the art (e.g. U.S. Pat. Nos. 3,669,103 and 3,670,731) that carboxylic polyelectrolytes may be cross-linked to form materials commonly referred to as superabsorbents. These materials are used to enhance the absorbency of disposable absorbent articles. Superabsorbent polymer may be coated (continuous or discontinuous coatings) on various materials (see U.S. Pat. No. 4,076,673). A layer of superabsorbent particles can be bound to a fibrous substrate using the inherent tackiness of a water swollen superabsorbent as described in U.S. Pat. No. 3,686,024. Thermally-activated adhesive binders may also be used as described in EP 0 641 835 A1. U.S. Pat. No. 5,128,082 teaches the fabrication of a superabsorbent-containing web in which the superabsorbent granules are deposited between two layers of fiber, with a latex bonding agent applied to each side of the sandwich structure to stabilize the web and bind the granules. U.S. Pat. No. 5,071,681 discloses preparing an airlaid fibrous web and applying a water-insoluble binder to one surface and a water soluble polymer capable of forming a superabsorbent to the other surface of the web. In U.S. Pat. No. 4,444,830, liquid superabsorbent precursor solution is chemically foamed and applied to a base fluffing material and the coated fluffing material is dried, disintegrated and mechanically worked into a fibrous fluff matrix which contains absorbent polymer platelets distributed throughout the matrix.

Adhering highly water-swollen superabsorbent granules to fibrous substrates as described for example in U.S. Pat. No. 3,686,024 causes a processing disadvantage because a considerable amount of water must be removed from the absorbent structure prior to use. Thermally bonding the particles to the fibers in a web entails a separate processing step of combining the adhesive with the granules before they are spread onto or mixed with the fibrous substrate and heated to fuse the thermal adhesive. Spraying a dilute solution of liquid superabsorbent precursor onto an airlaid web causes superabsorbent penetration into the web so that the superabsorbent polymer is less a discrete layer than a coating on the fibers of the web. Adding superabsorbent granules to a web between two or more fiber distributor heads and spraying with latex bonding agent embeds the granules in the web and precludes formation of a discrete layer of superabsorbent on the bottom of an airlaid web. It is recognized by those skilled in the art, that when superabsorbent particles are mixed with fibers, either bonded or unbonded, there is a competition for fluid between the superabsorbent and the surrounding fibrous structure which prevents the superabsorbent from achieving its full absorption potential. The present invention avoids these limitations by localizing superabsorbent particles to a discrete but integral layer.

Applicants have now discovered that it is desirable to bond a distinct layer of superabsorbent granules to one side of an absorbent structure.

SUMMARY OF THE INVENTION

Figure 1A:
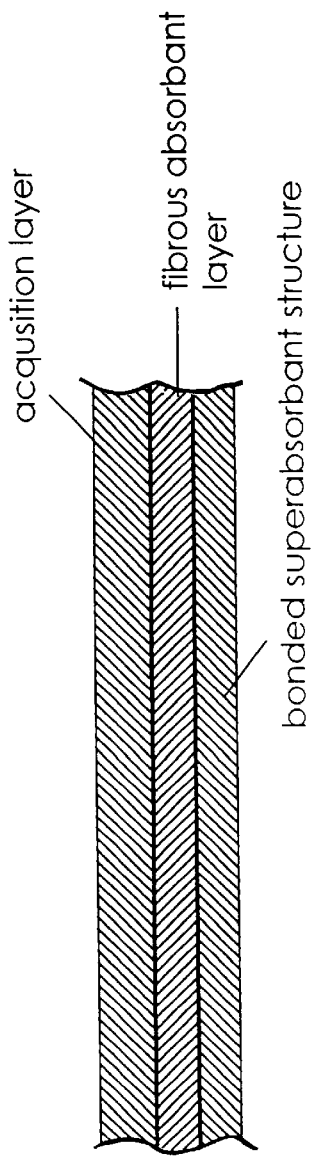
FIG. 1A is a diagram showing a structure of a superabsorbent roll good prepared according to one embodiment of the invention.

It has now been discovered that the superabsorbent polymer material need not be dispersed throughout the absorbent composite for the superabsorbent to perform its intended function. In fact, having the superabsorbent concentrated in a separate layer most removed from the source of liquid insult allows a more efficient utilization of the fibrous material in the absorbent composite for initially imbibing and then transporting the fluid. In a preferred embodiment of the invention, the integral layer of superabsorbent particles is applied in a discontinuous manner to facilitate fluid transport out of the acquisition/distribution layer. The pattern of discontinuity is not critical and may be accomplished by means known in the art such as by masking areas of a particle distributor head or by silk screen type printing of the latex binder such that particles adhere only in the areas coated with binder. Thus, less total fiber is needed to achieve the same level of performance relative to certain conventional products.

Accordingly, the present invention relates to a superabsorbent roll good suitable for use in disposable absorbent products, which contains a distinct superabsorbent layer comprising bonded superabsorbent polymer particles.

The present invention further relates to a method of making the roll good of the invention containing the superabsorbent layer of the invention.

DETAILED DESCRIPTION OF THE INVENTION

All patents, patent applications and references cited herein are hereby incorporated by reference in their entirety. In case of any inconsistency, the present disclosure governs.

The present invention relates to a superabsorbent roll good suitable for use in disposable absorbent products, which contains a distinct superabsorbent layer comprising bonded superabsorbent polymer particles. Typically, the layer of superabsorbent particles is bonded to the surface of a fibrous absorbent layer, such as for example an air laid nonwoven.

When used in a disposable absorbent product, such as a diaper or a feminine hygiene product, the superabsorbent layer of the invention is bonded to a fibrous absorbent layer and is located on that surface of the product, which is intended to be away from the wearer of the absorbent product.

The superabsorbent layer of the invention comprises superabsorbent polymer particles and a water soluble or a water dispersible polymeric binder. The superabsorbent layer does not normally contain any added fibers, but may contain those which may have been normally protruding from the plane of the surface of the fibrous structure and those around depressions in the surface into which superabsorbent granules could fall. The term "superabsorbent polymer particle" is intended to include any particulate form of superabsorbent polymer, including irregular granules, spherical particles (beads), staple fibers and other elongated particles. The term "superabsorbent polymer" refers to a normally water-soluble polymer which has been cross-linked prior to forming the superabsorbent layer of the invention.

It is known from U.S. Pat. Nos. 3,669,103 and 3,670,731 to crosslink carboxylic polyelectrolytes to create hydrogel-forming materials, now commonly referred to as superabsorbents, and to use such materials to enhance the absorbency of disposable absorbent articles. It is also known from U.S. Pat. Nos. 3,980,663 and 4,076,673 to add crosslinkers to solutions of carboxylated polyelectrolytes and dry and cure the polymer to a superabsorbent. The superabsorbent polymer granules useful in the practice of this invention are commercially available from a number of manufacturers, such as Dow Chemical (Midland, Mich.), Stockhausen (Greensboro, N.C.), and Chemdal (Arlington Heights, Ill.). Conventional granular superabsorbent polymer is based on poly(acrylic acid) which has been crosslinked during polymerization with any of a number of multi-functional comonomer crosslinking agents well-known in the art. Representative of these crosslinking agents are N,N'-methylenebisacrylamide, triallyl amine, and 1,1,1-trimethylolpropane triacrylate. To render the crosslinked poly(acrylic acid) highly water swellable, about 50–80 percent of the carboxylic groups are in the form of the sodium, potassium or ammonium salt. Superabsorbent polymer granules can also be prepared by crosslinking suitable water-soluble polymers after polymerization, but this approach is ideally suited for the preparation of a water-swellable binder from a water-soluble polymer. The water soluble and water swellable polymers useful in the practice of this invention generally may be any physiologically compatible, hydrophilic polymer. According to one embodiment of the present invention, a carboxylic polyelectrolyte may be used.

In one preferred embodiment, polyelectrolytes useful in the invention are ammonium or alkali metal salts of homopolymers of acrylic or methacrylic acid and copolymers with one or more ethylenically unsaturated comonomers.

In one embodiment, the polyelectrolyte is a partially saponified polyacrylate polymer. Before the saponification, the polymer may be prepared by reacting a mixture of monomers which may comprise (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl group has from 1 to 4 carbons.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, and 4-hydroxy butyl acrylate.

The olefinically unsaturated carboxylic acids useful in this invention are mono- or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

A list of applicable polymers which could be prepared from readily available monomers and converted into their salt form is as follows: acrylic acid—acrylate copolymers; acrylic acid—acrylamide copolymers; acrylic acid—olefinic copolymers; polyacrylic acid; acrylic acid—vinyl aromatic copolymers; acrylic vinyl ether copolymers; acrylic acid—vinyl acetate copolymers; acrylic acid—vinyl alcohol copolymers and copolymers of methacrylic acid with all the above comonomers.

In one preferred embodiment of the invention, the carboxylic polyelectrolyte is the half sodium salt of the alternating copolymer of an alpha-olefin and maleic anhydride, where the alpha olefin is ethylene, propylene, 1-butene, isobutylene, styrene, or mixtures of two or more thereof. In another preferred embodiment, the carboxylic polyelectrolyte is poly(acrylic acid) or a copolymer of acrylic acid with an ethylenically unsaturated monomer, in which the acid moieties are 40–90 percent neutralized with sodium hydroxide.

Other hydrophilic polymers may also be employed, such as acrylic copolymer and starch/graft copolymers. Also useful are water-insoluble alkali salts of saponified, gelatinized starch/polyacylonitrile graft polymers taught in U.S. Pat. Nos. 3,997,484 and 4,405,387.

Cross-linking agents that may be used for preparing the superabsorbent polymeric materials of the invention are well known in the art.

Illustrative examples of the polyfunctional cross-linking agents useful in this invention to convert the above polyelectrolytes into water-swellable polymers are set forth in U.S. Pat. Nos. 2,929,154; 3,224,986; 3,332,909; and 4,076,673 incorporated herein by reference. These polyfunctional cross-linking agents are generally known as polyamide-polyamine epichlorohydrin adducts. Similar cross-linking agents such as commercially available Kymene 557 and Polycup 172 (obtained from Hercules Incorporated, Wilmington, Del.). The structure of these adducts is well known and is described in M. E. Coor et al., *Journal of Applied Polymer Science*, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as cross-linking agents are monomeric amine-epihalohydrin adducts. Sulfonium zwitterions described in U.S. Pat. Nos. 3,660,431; 3,749,737; and 3,749,738, incorporated herein by reference, may also be used.

The cross-linking agents may be used in an amount from about 0.05 to about 5.0 percent based on the weight of the polyelectrolyte used. This is generally sufficient to cause the polyelectrolyte to become lightly cross-linked. However, a person of skill in the art may adjust this range for each polyelectrolyte in order to optimize the absorbency of the final cross-linked material by using routine experimentation based on the guidance in the present specification and the general knowledge in the art.

Water-swellable (superabsorbent) polymer particulates used to prepare the absorbent layer of the present invention are bonded with a polymeric binder. The term "polymeric binder" refers to any compound capable of bonding the superabsorbent granules to each other and/or to the fibrous absorbent layer. Superabsorbent particles of the superabsorbent layer may be bonded using the water soluble polymers with added crosslinkers which can themselves become a type of superabsorbent binder, latex bonded, and/or thermally-bonded.

A natural or synthetic latex may be used as a binder. In a preferred embodiment, the latex has a minimum film-forming temperature at or below room temperature. Examples of suitable latex binders are polymers and copolymers of alkylacrylate, vinyl acetate and styrene-butadiene. The advantages of using latex as a binder in the present invention were unexpected since U.S. Pat. No. 5,128,082 teaches that the application of a latex binder to the web can reduce the absorption by the superabsorbent particles.

The latex is generally used at from about 10 gsm latex per 160 gsm superabsorbent articles to about 80 gsm latex per 160 gsm superabsorbent particles, preferably from about 20 to about 40 gsm latex per 160 gsm superabsorbent particles.

A thermally-bonded superabsorbent layer may contain thermoplastic fibers or powder, which are well known in the art, and which are known to provide bonding upon heating to the melting point of the thermoplastic fiber or powder.

The polymeric binder suitable for use in the present invention may be a carboxylic polyelectrolyte in admixture with a cross-linking agent, which cross-linking agent has the property of reacting with carboxyl or carboxylate groups of the polyelectrolyte. The polymeric binder may also be a natural or synthetic latex having a minimum film-forming temperature at or below room temperature. The polymeric binder may also be a mixture of a crosslinkable carboxylic polyelectrolyte solution and a latex. This mixture exhibits the properties of both, i.e., the absorbency of the crosslinked polyelectrolyte and the flexibility of the rubbery polymer. The dispersed rubbery phase may facilitate bending and flexing of the superabsorbent coating without shattering.

Any other combination of above-described polymeric binders may be used in the present invention.

The superabsorbent layer of the invention may be prepared according to the following methods.

In one embodiment of the invention, a layer of superabsorbent particles is applied using methods known in the art onto the surface of a sheeted fiber material. A water soluble or water dispersible binder is then applied (e.g. sprayed or doctored) onto the layer of superabsorbent particles. Prior to application, the binder may be foamed to, for example, from about 1.5 to about 10 times its original volume, and preferably from about three to four times its original volume. This mode of application generally finds use in laboratory conditions.

In another embodiment of the invention, the superabsorbent polymer particles are mixed with the water soluble or water dispersible binder and then applied on to the surface of a sheeted fiber material. Alternatively, the binder may be first foamed, and then superabsorbent particles may be added to the foam immediately before application to the fiber material. This mode of application is suitable for continuous application and is therefore useful for large-scale production.

In one embodiment of the invention, the foamed water-soluble binder is mixed with a crosslinker suitable for crosslinking carboxylic polyelectrolytes to a superabsorbent material upon drying and curing.

In one embodiment of the invention, the superabsorbent roll good has a structure as shown in FIG. 1A. This structure contains a fibrous absorbent layer to which a superabsorbent layer is bonded on one side and the acquisition layer is bonded on the other side. The acquisition layer may be as generally known in the art. In one embodiment, the acquisition layer contains synthetic fibers selected from the group consisting of polyester, polyamide, and polyolefin. The synthetic fibers may be bonded with a latex polymeric binder or a thermoplastic binder fiber or thermoplastic binder powder or combination thereof. Alternatively, the acquisition layer may contain stiffened cellulosic fibers bonded with a latex polymeric binder or a thermoplastic binder fiber or thermoplastic binder powder or combination thereof.

Figure 1B:
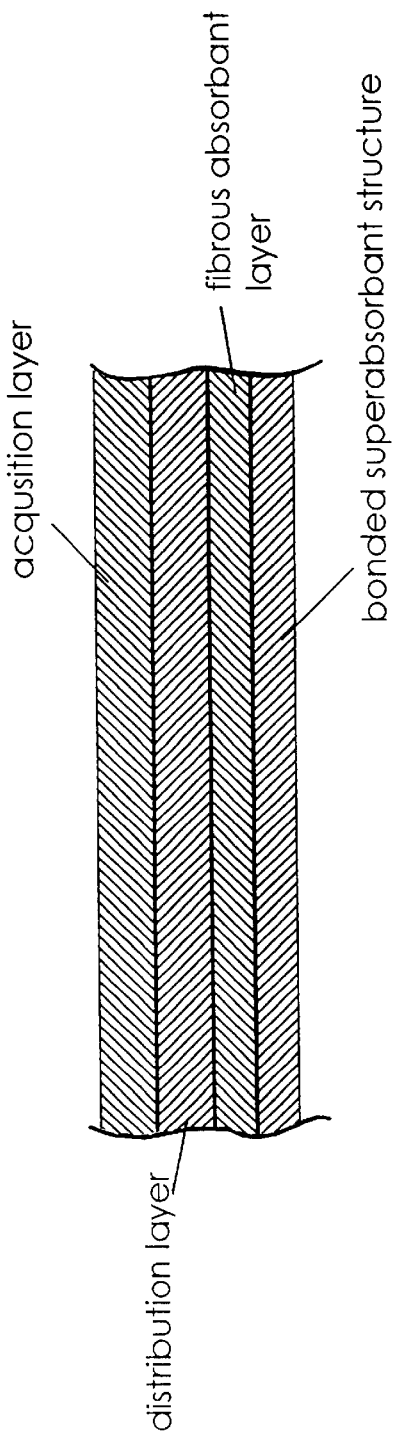
FIG. 1B is a diagram showing a structure of a superabsorbent roll good prepared according to one embodiment of the invention.

In another embodiment of the invention, the superabsorbent roll good of the invention contains a distribution layer located between the acquisition layer and the integral layer of superabsorbent particles, for example as shown in FIG. 1B. The distribution layer may be as generally known in the art. For example, the matrix fibers of the distribution layer may be (i) fluff cellulose fibers (e.g. Buckeye Foley fluff available from Buckeye Technologies, Inc., Memphis, Tenn.), (ii) chemically modified fluff cellulose (e.g. cross-linked cellulose) or highly purified cellulose (e.g. Buckeye HPF), or (iii) blends thereof. The fibers may be latex-bonded fibers, thermally-bonded fibers or a combination thereof.

Superabsorbent roll goods of the present invention may be used to make disposable absorbent products such as diapers, feminine hygiene products and incontinence products. When used in a superabsorbent product, the superabsorbent layer of the invention is located away from the skin of the wearer, i.e., away from the intended fluid insult. The insult side of such disposable absorbent product preferably contains an acquisition layer of bonded cellulosic or synthetic fibers bonded with thermoplastic binder fibers or powder, a latex binder, or a combination thereof.

One of the advantages of the present invention is that it solves the traditional problem of superabsorbent particle containment in a fibrous structure during handling and processing. The invention provides the absorbent component of a disposable absorbent article in a roll form so that the manufacturer of the final absorbent product need not operate fiber opening, web-forming, and superabsorbent metering equipment in order to produce the product. Thus, the invention facilitates the manufacturing of disposable absorbent products.

Another advantage of the invention is that the superabsorbent material is present in the absorbent structure in a discrete but integral layer whereby the influx of fluid into the acquisition layer and through the middle or distribution layer is not restricted and the swelling of the superabsorbent itself is not impeded by being entrapped in a fiber matrix. Essentially all the superabsorbent particles are exposed to the binder so the particles are well-contained on the web and the superabsorbent addition may be done as a part of the web-forming process or may be done in a separate line from the forming equipment. Performing this operation remote from the web-forming equipment could be an advantage by avoiding fouling with the superabsorbent dust which can result in considerable expensive down-time.

The invention is further described in the following non-limiting examples.

EXAMPLES

Experimental Procedures
Preparation of the Superabsorbent Polymer Precursor Solution The sodium half salt of poly(isobutylene-co-maleic anhydride) from Kuraray International (ISOBAM-10, lot no. 825271) is prepared in a 1000 ml resin flask equipped with paddle stirrer, reflux condenser, temperature controller, and heating mantle at 25% solids by suspending 154 g (1.0 mol) of copolymer in 582 grams of distilled water containing 0.3 grams of Neodol 25-9 (non-ionic surfactant) by Shell Chemical Company (Houston, Tex.). Sodium hydroxide in the pill or bead form (40.0 grams, 1.0 mol, from Aldrich Chemical (Milwaukee, Wis.) lot no. 02420HQ) is added to the slurry and the temperature is raised to 85° C. Heating and stirring is continued until the polymer dissolves, about four hours. The prepared solution may be used as a polymeric binder for superabsorbent granules, or it may be converted into superabsorbent granules using methods known in the art.

Preparation of Superabsorbent Precursor Foam

The 25% solution of half-neutralized ISOBAM-10 (50.0 grams) is diluted to 10% solids with 125 grams distilled water, and 0.13 grams of sodium lauryl sulfate (anionic surfactant) is added to stabilize the foam. The crosslinker (KYMENE 557 by Hercules Incorporated (Wilmington, Del.) 1.0% by weight polymer (1.25 grams) is added and the solution is stirred rapidly with a perforated paddle with a sub-surface stream of nitrogen to facilitate foaming. The stirring is continued until the foam volume is about three times the original liquid volume. The foam is ready to use or may be blended with a latex to flexibilize the dried and cured polymer. If a latex is added, the water in the latex may be subtracted from the distilled water in the recipe.

Coating of Non-wovens with Foam

The weight of foam calculated to yield the desired polymer loading is spread evenly on the non-woven and dried at 125° C. in a laboratory convection oven. For 40 gsm on a 14×14 inch pad, the total solids is 5.06 grams (50.6 grams of foam). During the drying step, the crosslinker is activated and the polymer becomes superabsorbent. The commercial granular superabsorbent used in this experiment is FAVOR® SXM 70 by Stockhausen, a surface-crosslinked acrylic acid-based conventional superabsorbent.

Saturated Capacity

Samples are cut into two inch squares, placed in labeled disposable weighing dishes, and weighed to the nearest centigram. Excess saline (0.9% NaCl) is added and absorption is allowed to continue for thirty minutes. The excess saline is poured out and the dish is propped on its side for five minutes. Any additional drainage is poured out and the dish and pad are weighed. The saturated capacity of the pad (grams saline absorbed per gram of pad) equals the total weight of the dish and wet pad minus the weight of the dish and dry pad divided by the weight of the dry pad.

Retention Capacity

The pads from the saturated capacity test are placed on four layers of dry pulp sheet (functioning as blotter paper) and pressed under a load of 0.9 psi for five minutes. The pressed pads are weighed and the retention capacity is the weight of the pressed pad minus the weight of the dry pad divided by the weight of the dry pad.

Acquisition Rate

Four inch square pads are wrapped with a standard diaper cover-stock material and placed under a 0.3 psi load. At the center of the weight is 1.5 inch diameter target zone equipped with a clear addition tube four inches high. A 50 ml insult of 0.9% saline is poured into the cylinder and the time for it to be absorbed is recorded. This is repeated twice more at one minute intervals. The rate expressed in ml/sec of the third insult is designated as the acquisition rate for the sample.

Multiple Dose Rewet

The diaper is laid flat on the laboratory bench top and insulted in the middle with 50 ml of 0.9%NaCl poured from a graduated cylinder. After 20 minutes, a tared stack of 11 cm diameter Whatman No. 3 filter papers (10–12 papers) is placed on the target area and pressed for one minute under a pressure of 0.8 psi applied by a 9 cm diameter weight. The weight of saline captured by the filter paper is the rewet. The procedure is repeated two more times using additional sheets of filter paper since rewet usually goes up after repeated insults.

Experimental Results

All the controls and examples, except for the commercial product Zorbcor, were made on a typical laboratory airlaid web-forming apparatus in which the mixture of acquisition layer fiber and binder fiber were formed first followed by the mixture of fluff and binder fiber.

Control 1 (Zorbcor® 5902 supplied by Buckeye Technologies Inc., Memphis, Tenn.) has a total 450 gsm. It includes 183 gsm of granules substantially uniformly distributed throughout the pad. This material is ordinarily intended for incontinence products requiring a very high absorption capacity. Control 1 was compared to pads made in the laboratory which contained 150 gsm of fiber (50 gsm of 90/10 crosslinked cellulose/bicomponent binder fiber layer and 100 gsm of 95/5 fluff/bicomponent binder fiber layer). The bicomponent fiber (Type T-255 from Hoechst-Trevira (Charlotte, N.C.) is a low melting polyethylene sheath on a polyester core. The newly-formed absorbent structure was heated to about 160° C. to fuse the binder fiber. To the fluff side, 160–180 gsm of superabsorbent granules was applied followed by several binder formulations to give a total of 350 gsm. The particular latex used in these examples was RHOPLEX® HA-8 supplied by Rohm and Haas (Philadelphia, Pa.). Any other latex typically used in non-woven manufacture would also be effective. The superabsorbent was FAVOR® SXM70, a surface crosslinked granular material supplied by Stockhausen Inc. (Greenboro, N.C.). For Examples 4 and 5, the procedures of Examples 2 and 3 were repeated except that 180 gsm of granular superabsorbent was spread on the airlaid non-woven before the application of the binders. All the controls and examples, except for the commercial product Zorbcor, were made on a typical laboratory airlaid web-forming apparatus in which the mixture of acquisition layer fiber and binder fiber were formed first followed by the mixture of fluff and binder fiber.

Control 3 (Vizorb® 3900 from Buckeye Technologies) is 120 gsm (30 gsm superabsorbent) and is normally intended for use in feminine hygiene articles. Vizorb was compared to a pilot line produced airlaid which was 80 gsm fluff and styrene-butadiene latex binder. The smooth (wire) side was treated with superabsorbent granules and foam/latex.

less fiber. Example 3 (latex binder for the superabsorbent) also has less superabsorbent than Control 1. Example 5 with comparable superabsorbent loading to Control 1 exhibits significant greater capacity. The acquisition rate (a measure of the porosity of the absorbent pad, particularly of the upper portion) is greater in the examples than the commercial controls, which controls lack a discrete acquisition layer and in which the superabsorbent granules are evenly distributed throughout the pad. Even Example 6, which does not have the discrete acquisition layer, has a higher acquisition rate than Control 3, indicating that the homogeneous distribution of superabsorbent particles in Control 3 may be inhibiting acquisition compared to having the particles all bonded to the lower surface of the absorbent structure.

For Control 4 and Examples 7–9, the procedure of Examples 1–3 was repeated, except instead of the stiffened cellulose fiber acquisition layer, a crimped polyester staple fiber (T-224 by Hoechst-Trevira of Salisbury, N.C.) is blended with the bicomponent fiber to form, after heating to 160° C., a synthetic acquisition layer.

TABLE 2

Working Examples 7–9

| Working Example | gsm Fiber | gsm SAP Granules | gsm SAP Foam Solids | gsm Latex Solids | Sat. Cap. g/g | 0.9 psi Retention g/g | Acquisition Rate ml/sec |
|---|---|---|---|---|---|---|---|
| Control 4 | 150 | | | | 19.2 | 0.5 | 2.1 |
| Example 7 | 150 | 160 | 40 | | 18.3 | 8.0 | 2.8 |
| Example 8 | 150 | 160 | 30 | 10 | 25.8 | 13.2 | 3.1 |
| Example 9 | 150 | 160 | | 40 | 29.1 | 29.1 | 6.6 |

The crimped polyester/bicomponent integral acquisition layer exhibits outstanding acquisition rate compared to the stiffened cellulose acquisition layer used in Control 2 and Examples 1–5 of Table 1. Since Examples 7–9 acquire fluid faster than Control 4, the layer of superabsorbent also appears to be assisting by draining the acquisition and middle layers.

Capacity is not the only critical property in a diaper design. For comfort and skin-wellness, the product should keep the skin dry by exhibiting low rewet under pressure after multiple insults. Prototype diaper constructions are prepared by hand and tested for multiple dose rewet and acquisition (penetration) rate using 50 ml insults of 0.9 percent sodium chloride. To make a (4 inches by 14 inches) diaper for testing, a piece of carrier tissue or airlaid is placed on a polyethylene backing sheet, followed by the

TABLE 1

Working Examples 1–6

| Working Example | gsm Fiber | gsm SAP Granules | gsm SAP Foam Solids | gsm Latex Solids | Sat. Cap. g/g | 0.9 psi Retention g/g | Acquisition Rate ml/sec |
|---|---|---|---|---|---|---|---|
| Control 1 | 267 | 183 | | | 20.1 | 13.1 | 0.3 |
| Control 2 | 150 | | | | 25.5 | 1.0 | 1.1 |
| Example 1 | 150 | 160 | 40 | | 32.3 | 17.0 | 0.9 |
| Example 2 | 150 | 160 | 30 | 10 | 24.8 | 17.5 | 1.0 |
| Example 3 | 150 | 160 | | 40 | 25.7 | 14.8 | 1.6 |
| Example 4 | 150 | 180 | 30 | 10 | 32 | 21.6 | 1.4 |
| Example 5 | 150 | 180 | | 40 | 33.2 | 24.6 | 1.6 |
| Control 3 | 90 | 30 | | | 20.9 | 5.8 | 0.3 |
| Example 6 | 80 | 30 | 10 | 5 | 23.1 | 5.4 | 0.7 |

Examples 1–3 exhibit higher absorbency per gram than the commercial sample Control 1, while employing much acquisition/distribution layer with the superabsorbent adhered thereto and covered with a conventional thermally-bonded polypropylene carded web coverstock, available from PGI Nonwovens of Landesville, N.J. under the brand name of Soft Touch by Fiber Tech, and the entire construction is edge-sealed to make a rectangular diaper without any elastics or leg cuffs. A commercial diaper made by Proctor & Gamble under the name of PAMPERS Baby Dry 3 was tested along side the laboratory prototypes after having the leg cuffs and elastics removed so it would lie flat. In example 10,250 gsm of superabsorbent is bonded to the bottom of an acquisition/distribution layer using 25 gsm of a poly(vinyl acetate) copolymer latex (AirFlex 108 from Air Products and Chemicals, Inc. of Allentown, Pa.) leaving a one half inch wide open strip in the SAP layer running the length of the diaper. The ADL is 34 gsm of crimped polyester bonded with 6 gsm of a poly(vinyl acetate) copolymer latex (AirFlex 192 from Air Products and Chemicals, Inc.) over 40 gsm of 90/10 thermally-bonded mixture of cellulose fluff (HPF mercerized pulp available from Buckeye Technologies, Inc. of Memphis, Tenn.) and Type T-255 bicomponent fiber from Hoechst-Trevira (Charlotte, N.C.). The acquisition layer with adhered superabsorbent was tested over a 50 gsm cellulose fluff-bicomponent fiber airlaid distribution layer. Example 11 was similar except only 15 gsm of latex was used as SAP binder instead of 25 gsm. Example 12 was the same as Example 10 except the bottom distribution layer of the diaper (next to the polyethylene outer cover) was a piece of 30 gsm carrier tissue instead of 50 gsm airlaid.

TABLE 3

Working Examples 10–12

| Example | Diaper Basis Weight | Acquisition Rate ml/sec | Rewet 1 | Rewet 2 | Rewet 3 |
|---|---|---|---|---|---|
| 10 | 433 gsm | 4.8 | 0.2 | 2.3 | 12.3 |
| 11 | 423 gsm | 8.6 | 0.2 | 0.7 | 8.5 |
| 12 | 413 gsm | 6 | 0.1 | 1.1 | 8.7 |
| Control | 700 gsm | 2.9 | 0.2 | 1.5 | 6.3 |

Table 3 shows that diapers constructed according to the present invention, despite containing significantly less absorbent material, compare favorably to a successful commercial product in these tests of fluid handling.

What is claimed is:

1. an absorbent structure suitable for fabrication into disposable personal care articles comprising:
   (A) a fibrous absorbent layer; and
   (B) a discrete superabsorbent layer which is substantially free of fibers and includes superabsorbent polymer particles localized therein, wherein the discrete superabsorbent layer is integral with and inseparably bonded to the surface of the fibrous absorbent layer by a polymeric binder comprising a natural or synthetic latex having a minimum film-forming temperature at or below room temperature.

2. The absorbent structure of claim 1, wherein said superabsorbent layer is located on the side of the absorbent structure intended to be away from the wearer.

3. The absorbent structure of claim 1, wherein the superabsorbent layer comprises a granular carboxylic crosslinked polyelectrolyte.

4. The absorbent structure of claim 3, wherein the polyelectrolyte is selected from the group consisting of polymers and copolymers of poly(acrylic acid).

5. The absorbent structure of claim 1, further comprising an acquisition layer.

6. The absorbent structure of claim 5, further comprising a distribution layer.

7. The absorbent structure of claim 5, wherein the acquisition layer comprises synthetic fibers.

8. The absorbent structure of claim 7, wherein the synthetic fibers are polyester, polyamide, polyolefin, or a mixture thereof.

9. The absorbent structure of claim 7, wherein the synthetic fibers are bonded with a latex polymeric binder.

10. The absorbent structure of claim 7, wherein the synthetic fibers are bonded with a thermoplastic binder fiber or thermoplastic binder powder.

11. The absorbent structure of claim 10, wherein the synthetic fibers are bonded with a combination of a thermoplastic binder and a latex binder.

12. The absorbent structure of claim 5, wherein the acquisition layer comprises stiffened cellulosic fibers.

13. The absorbent structure of claim 12, wherein the stiffened cellulosic fibers are bonded with a latex polymeric binder.

14. The absorbent structure of claim 12, wherein the stiffened cellulosic fibers are bonded with a thermoplastic binder fiber or thermoplastic binder powder.

15. The absorbent structure of claim 5, wherein the acquisition layer comprises a combination of synthetic fibers and cellulosic fibers bonded with latex, thermally bonded, or bonded with latex and thermally bonded.

16. The absorbent structure of claim 1, wherein the superabsorbent polymer particles are deposited in a discontinuous manner in the superabsorbent layer.

17. A disposable absorbent hygiene article prepared from the absorbent structure of claim 1.

18. The disposable absorbent hygiene article of claim 17, wherein the article is a diaper.

19. The disposable absorbent hygiene article of claim 17, wherein the article is a article is a sanitary napkin.

20. The disposable absorbent hygiene article of claim 17, wherein the article is an adult incontinent product.

21. An absorbent structure suitable for fabrication into disposable personal care articles comprising:
   (A) a fibrous absorbent layer; and
   (B) a discrete superabsorbent layer which is substantially free of fibers and includes superabsorbent polymer particles localized therein, wherein the discrete superabsorbent layer is integral with and inseparably bonded to the surface of the fibrous absorbent layer by a polymeric binder comprising a mixture of a natural or synthetic latex having a minimum film-forming temperature at or below room temperature, a carboxylic polyelectrolyte, and a crosslinking agent having the property of reacting with carboxyl or carboxylate groups.

22. The absorbent structure of claim 21, wherein said crosslinking agent is a poly-functional crosslinking compound.

* * * * *